United States Patent [19] [11] Patent Number: 5,043,466
Shepard [45] Date of Patent: Aug. 27, 1991

[54] PREPARATION OF CYCLOHEXANOL DERIVATIVES AND NOVEL THIOAMIDE INTERMEDIATES

[75] Inventor: Robin G. Shepard, Windsor, England

[73] Assignee: John Wyeth & Bro., Limited, Maidenhead, England

[21] Appl. No.: 471,187

[22] Filed: Jan. 26, 1990

[30] Foreign Application Priority Data

Feb. 1, 1989 [GB] United Kingdom ................ 8902209

[51] Int. Cl.$^5$ .......................................... C07C 255/00
[52] U.S. Cl. ..................................... 558/371; 564/74; 564/171; 564/336
[58] Field of Search ........................ 564/336, 74, 171; 558/371

[56] References Cited

U.S. PATENT DOCUMENTS 3,060,236 10/1962 Kollar et al. ........................ 558/371
3,162,674 12/1964 Middleton ........................... 558/371
3,325,544  6/1967 Moffett .............................. 558/371
3,372,193  3/1968 Moffett .............................. 558/371
3,743,669  7/1973 Hillman et al. ..................... 558/371
3,803,203  4/1974 Vincent et al. ..................... 558/371
4,820,858  4/1989 Isaacs et al. ....................... 558/371

FOREIGN PATENT DOCUMENTS 0112669 7/1987 European Pat. Off. .

OTHER PUBLICATIONS

Kaiser et al., J. Org. Chem. 33, 4275–4278 (1968).
Sauvetre et al., Tetrahedron Letters, 44, 3949–3952 (1976) (French, Translation not available).
Treves et al., J. Am. Chem. Soc., 74 46–48 (1952).

Primary Examiner—Richard L. Raymond
Assistant Examiner—Scott C. Rand
Attorney, Agent, or Firm—Arthur G. Seifert

[57] ABSTRACT

The preparation of compounds having the formula I

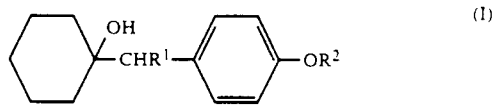

where $R^1$ is —CN, —CO—N(CH$_3$)$_2$ or —C-S—N(CH$_3$)$_2$ and $R^2$ is hydrogen, methyl or a removable protecting group is carried out by condensing a compound having the formula

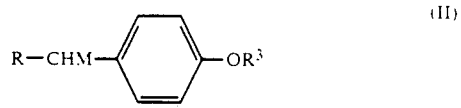

where M is lithium, sodium, potassium or halomagnesium and $R^3$ is methyl or a removable protecting group in a solvent comprising 80–100% of one or more hydrocarbons and 0–20% of one or more ethers.

The solvent enables less inconvenient reaction temperatures to be used and higher yields to be obtained. Compounds (I) are new per se where $R^1$ is —CS—N(CH$_3$)$_2$. Compounds (I) are chemical intermediates for preparing N,N-dimethyl-2-(1-hydroxycyclohexyl)-2-(4-hydroxyphenyl or 4-methoxyphenyl) ethylamine and pharmaceutically acceptable salts thereof. These end products are antidepressants.

14 Claims, No Drawings

PREPARATION OF CYCLOHEXANOL DERIVATIVES AND NOVEL THIOAMIDE INTERMEDIATES

The invention relates to a process for the preparation of N,N-dimethyl-2-(1-hydroxycyclohexyl)-2-(4-hydroxyphenyl or 4-methoxyphenyl)ethylamine or pharmaceutically acceptable salts thereof. These compounds are pharmaceutically useful, particularly as antidepressants. The invention also relates to a process for the preparation of cyclohexanol derivatives useful as chemical intermediates for the preparation of the aforesaid pharmaceutically useful compounds. The invention also relates to novel thioacetamide derivatives useful as such chemical intermediates.

EP 0112669B discloses the preparation of various 2-aryl-2-(1-hydroxycyclohexyl)ethylamine derivatives via α-aryl-α-(1-hydroxycyclohexyl)acetonitriles or α-aryl-N,N-dimethyl-α-(1-hydroxycyclohexyl)acetamides as chemical intermediates. These chemical intermediates were prepared by condensing α-arylacetonitriles or α-aryl-N,N-dimethylacetamides with cyclohexanone. The condensation was carried out by reacting the starting nitrile or amide in the form of its lithium derivative with cyclohexanone in a solvent essentially comprising tetrahydrofuran at low temperatures, namely about −50° C. or about −70° C. The need for plant for operating at very low temperatures is a disadvantage of the method. Moreover the yields quoted for the condensation reaction are below 50%.

The present invention is based upon the discovery that hydrocarbon solvents are advantageously used as the reaction medium for the condensation in the preparation of intermediates for the aforesaid pharmaceutically useful compounds. Although the condensation may be carried out in hydrocarbon solvents at low temperatures the invention has the advantage that such inconvenient temperatures can be avoided. Indeed the reaction may be carried out, for example, at ambient temperatures. A second advantage of the invention is that it enables higher yields to be obtained. For instance α-(1-hydroxycyclohexyl)-α-(4-methoxyphenyl)acetonitrile was prepared in a yield of about 30% in the prior art process of Example 1 of EP 0112669B and in a yield of 79% in Example 1 below carried out in accordance with the invention. The invention also has the advantage that novel thioacetamide derivatives may be obtained as chemical intermediates for the aforesaid pharmaceutically useful compounds. Such thioamides cannot be prepared in practice unless hydrocarbon solvents are used.

The present invention provides a first process for the preparation of a compound having the formula I

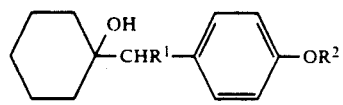

wherein $R^1$ is —CN, —CO—N(CH$_3$)$_2$ or —C-S—N(CH$_3$)$_2$ and $R^2$ is hydrogen, methyl or a removable protecting group for phenolic hydroxy, wherein a compound having the formula II

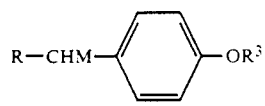

where $R^1$ is as defined above, M is lithium, sodium, potassium or halomagnesium and $R^3$ is methyl or a removable protecting group for phenolic hydroxy is condensed with cyclohexanone in a solvent comprising 80% to 100% by weight of one or more hydrocarbons and 0% to 20% by weight of one or more ether, preferably in a solvent consisting entirely of one or more hydrocarbons.

The direct product of the condensation is a compound having the formula III

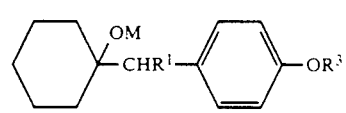

Neutralization of the reaction mixture yields a compound having the formula I wherein $R^2$ is the same as $R^3$ or, if a removable protecting group is removed during neutralisation, a compound having the formula I wherein $R^2$ is hydrogen. Alternatively a compound having formula I wherein $R^2$ is hydrogen may be prepared by carrying out the process of the invention and removing the removable protecting group as a subsequent step.

The compound having the formula II is normally prepared by generation from a compound having the formula IV

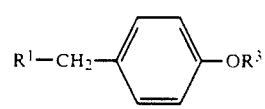

where $R^1$ and $R^3$ are as defined above in a solvent suitable for subsequent performance of the condensation reaction. Where M is Li, the base used to generate the compound having formula II is preferably lithium diisopropyl amide. Lithium diisopropyl amide is commercially available in solution in ethylbenzene. Where this is used the ethylbenzene may form part of the hydrocarbon solvent for the condensation reaction.

As examples of hydrocarbon solvents there may be mentioned cyclohexane, hexane or toluene. The solvent system used for the condensation preferably consists entirely of one or more hydrocarbons but may also contain a small proportion, namely up to 20% by weight, of one or more ethers. As example of ethers, diethyl ether and tetrahydrofuran may be mentioned.

The condensation according to the first process of the invention may be carried out at temperatures within the range of, for example, −70° C. to 40° C., preferably −30° C. to 30° C., advantageously 0° C. to ambient temperature. Where $R^2$ in the product of formula I is methyl, then a starting compound in which $R^3$ is methyl in formula II is used. This meaning of $R^3$ is appropriate where the ultimate end product to be prepared is N,N-dimethyl-2-(1-hydroxycyclohexyl)-2-(4-methoxyphenyl)ethylamine or a pharmaceutically acceptable salt thereof. However, a methyl group as $R^3$ may be used as a phenolic protecting group which is removed at any suitable stage after the condensation of the compound of formula II with cyclohexanone. In this case the protecting group can be removed by ether cleavage in known manner. As examples of alternative protecting groups that may be used where N,N-dimethyl-2-(1-hydroxycyclohexyl)-2-(4-hydroxyphenyl)ethylamine or a pharmaceutically acceptable salt is to be prepared as the ultimate end product, there may be mentioned trialkylsilyl or benzyl. The benzyl group may be removed by hydrogenation. The trialkylsilyl group will normally be removed when the neutralisation is carried out during the work up of the condensation reaction mixture.

The compounds having the formula I where $R^1$ is —CS—N(CH$_3$)$_2$ are novel compounds provided by this invention. For their preparation the use of halomagnesium as M is particularly recommended. M is preferably lithium where $R^1$ is —CN or —CO—N(CH$_3$)$_2$.

The present invention also provides a second process. This is for the preparation of compound having the formula V

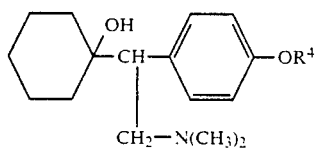

(V)

wherein $R^4$ is methyl or hydrogen or a pharmaceutically acceptable salt thereof. According to this process a compound having the formula I

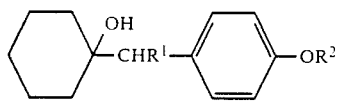

(I)

where $R^1$ and $R^2$ are as defined above is prepared according to the aforesaid first process of the invention and is subjected to reduction to prepare an amine and, where $R^1$ is —CN, the resultant —CH$_2$NH$_2$ group is subjected to methylation or reductive methylation to form the —CH$_2$N(CH$_3$)$_2$ group, where $R^2$ is a removable protecting group for phenolic hydroxy, the removable protecting group should be subjected to removal at any convenient stage in the process. The process may also include conversion of a free base form of the compound having formula V into a pharmaceutically acceptable salt, in particular by addition of an acid, or may include conversion of a salt form of a compound having formula V into the free base, in particular by treatment to subtract an acid. The process may also include separation of a compound having formula V in the form of a mixture of enantiomers so as to recover an individual enantiomer.

Where $R^1$ is —CS—N(CH$_3$)$_2$, in formula I, the reduction to form the amine may be carried out by contacting the thioamide with Raney nickel in a suitable solvent such as dioxan, tetrahydrofuran, ethyl alcohol, isopropyl alcohol, aqueous ethanol. Acetic acid may also be included in the reaction mixture and is preferably present.

Where $R^1$ is —CO—N(CH$_3$)$_2$ or —CN, the reduction may be carried out as described in EP 0112669B. Other steps such as separation of individual enantiomers and conversion of —CH$_2$NH$_2$ derived from —CN into —CH$_2$N(CH$_3$)$_2$ may also be carried out as described in EP 0112669B. The primary amine is preferably converted into its N,N-dimethyl derivative by reaction with formaldehyde and formic acid.

The compounds having the formula I are useful as pharmaceuticals, in particular as antidepressants and may be brought into combination or association with pharmaceutically acceptable carrier materials to form pharmaceutical compositions.

The invention is illustrated by the following Examples:

EXAMPLE 1

α(1-Hydroxycyclohexyl)-p-methoxyphenylacetonitrile

Lithium diisopropylamide was made from 1.6M butyl lithium in hexane (325 ml), diisopropylamine (73 ml) and toluene (300 ml) under an inert atmosphere of nitrogen. A solution of p-methoxyphenylacetonitrile (76.5 g) in toluene (75 ml) was added to the solution under nitrogen over 15 minutes whilst the internal temperature was maintained below 10° C. After a half hour a solution of cyclohexanone (46 g) in toluene (50 ml) was added over 15 minutes to the reaction mixture under nitrogen whilst the internal temperature was maintained below 10° C. After a further half hour the mixture was blown over onto an ice-cold mixture of 12N hydrochloric acid (100 ml) and water (1l). The crystalline material was filtered off and then taken up into dichloromethane. The solution was washed with water and dried. The solvent was replaced with di-isopropyl ether by distillation. After cooling, the product was filtered and dried in vacuo to yield 91 g (79% yield ) of the title compound.

EXAMPLE 2

N,N-Dimethyl-α-(1-hydroxycyclohexyl)-p-methoxyphenylthioacetamide

N,N-Dimethyl-p-methoxyphenylthioacetamide (20.9 g) in toluene was added to a solution of 1.45M isopropyl magnesium bromide in methyl t-butyl ether (80 ml) and toluene (400 ml) under an inert atmosphere of nitrogen whilst the internal temperature was maintained below 10° C. After 2 hours a solution of cyclohexanone (9.82 g) in toluene (50 ml) was added to the reaction mixture under nitrogen. After a further 15 minutes the mixture was blown over onto 1N hydrochloric acid (150 ml). The organic phase was washed, dried and evaporated. Recrystallisation of the residue from di-isopropyl ether gave the title compound (19.3 g, 64% yield), melting point 132° to 3° C.

Analysis

Found C,66.5%; H,8.2%; N,5.0%.

C$_{17}$H$_{25}$NO$_2$S requires C,66.5%; H,8.2%; N,4.6%.

EXAMPLE 3

N,N-Dimethyl-2-(1-hydroxycyclohexyl)-2-(4-methoxyphenyl)ethylamine

A solution of N,N-dimethyl-α-(1-hydroxycyclohexyl)-p-methoxyphenylthioacetamide in 5 ml per gram of thioamide in dioxan/acetic acid (9:1) is added to Raney nickel (20 grams per gram of thioamide) in 50 ml per gram of the thioamide of the same solvent at room temperature to 50° C. After 15 minutes to 10 hours the Raney nickel is filtered through kieselguhr and the solvent is evaporated under reduced pressure. The residue is partitioned between 2N sodium hydroxide solution and methylene chloride. The organic phase is dried and the solvent is evaporated. The residue is converted into the hydrochloride salt of the title compound using 4N isopropanolic hydrogen chloride.

A number of experiments have been carried out. The ratio of dioxan to acetic acid may vary from 50:1 to 2:1. The weight of Raney nickel used may vary from 5 to 50 grams per gram of the thioamide. The yields obtained range from about 50% to about 75%. It is particularly recommended to use a dioxan/acetic acid ratio of 19:1 and a Raney nickel/thioamide ratio of 50:1 and to allow a half hour at 50° C. for the reduction reaction.

I claim:

1. A process for the preparation of a compound having the formula

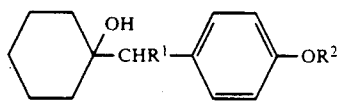
(I)

wherein $R^1$ is —CN, —CO—N(CH$_3$)$_2$ or —C-S—N(CH$_3$)$_2$ and $R^2$ is hydrogen, methyl or a removable protecting group for phenolic hydroxyl, said process comprising condensing a compound having the formula II

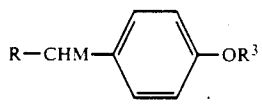
(II)

wherein $R^1$ is as defined above, M is lithium, sodium, potassium or halomagnesium and $R^3$ is methyl or a removable protecting group for phenolic hydroxy, with cyclohexanone in a solvent comprising 80% to 100% by weight of one or more hydrocarbons and 0% to 20% by weight of one or more ethers at temperatures of −40° C. to 40° C.

2. A process according to claim 1 wherein said solvent consists entirely of one or more hydrocarbons.

3. A process according to claim 1 wherein said solvent consists entirely of a hydrocarbon which is ethylbenzene or toluene.

4. A process according to claim 1 wherein $R^3$ is methyl.

5. A process according to claim 1 wherein $R^1$ is —CN.

6. A process according to claim 1 wherein the temperature is −30° C. to 30° C.

7. A process according to claim 1 wherein the temperature is 0° C. to ambient temperatures.

8. A process for the preparation of a compound having the formula

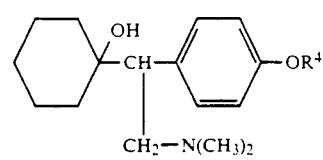
(V)

where $R^4$ is methyl or hydrogen, or a pharmaceutically acceptable salt thereof, comprising said process condensing a compound having the formula

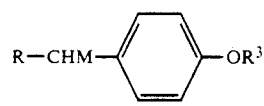
(II)

where $R^1$ is —CN, —CO—N(CH$_3$)$_2$ or —C-S—N(CH$_3$)$_2$, M is lithium, sodium, potassium or halomagnesium and $R^3$ is methyl or a removable protecting group for phenolic hydroxy, with cyclohexanone in a solvent comprising 80% to 100% by weight of one or more hydrocarbons and 0% to 20% by weight of one or more ethers at temperatures of −40° C. to 40° C.; and (b) subjecting the resultant compound having the formula

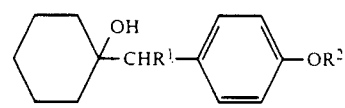
(I)

where $R^1$ is as defined above and $R^2$ is hydrogen, methyl or a removable protecting group for phenolic hydroxy, to reduction to prepare an amine and, where $R^1$ is —CN, subjecting the resultant —CH$_2$—NH$_2$ group to methylation or reductive methylation to form the —CH$_2$—N(CH$_3$)$_2$ group and, where $R^2$ is a removable protecting group for phenolic hydroxy, removing the removable protecting group at any convenient stage in the process.

9. A process according to claim 8 wherein said solvent consists entirely of one or more hydrocarbons.

10. A process according to claim 8 wherein said solvent consists entirely of a hydrocarbon which is ethylbenzene or toluene.

11. A process according to claim 8 wherein $R^3$ is methyl.

12. A process according to claim 8 wherein $R^1$ is —CN.

13. A process according to claim 8 wherein the temperature is −30° C. to 30° C.

14. A process according to claim 8 wherein the temperature is 0° C. to ambient temperatures.

* * * * *